United States Patent
Thramann et al.

(10) Patent No.: US 8,577,477 B2
(45) Date of Patent: Nov. 5, 2013

(54) ENDOTRACHEAL TUBE WITH A SELECTIVELY POSITIONAL ELECTRODE

(75) Inventors: Jeff Thramann, Longmont, CO (US); James Higgins, Phoenix, AZ (US)

(73) Assignee: ProNerve, LLC, Broomfield, CO (US)

( * ) Notice: Subject to any disclaimer, the term of this patent is extended or adjusted under 35 U.S.C. 154(b) by 128 days.

(21) Appl. No.: 12/813,745

(22) Filed: Jun. 11, 2010

(65) Prior Publication Data

US 2011/0306861 A1 Dec. 15, 2011

(51) Int. Cl.
- *A61N 1/00* (2006.01)
- *A61B 5/04* (2006.01)
- *A61B 18/04* (2006.01)

(52) U.S. Cl.
USPC ............ 607/124; 600/380; 600/546; 606/32; 607/115

(58) Field of Classification Search
USPC .................. 600/372–373, 380, 546; 606/32; 607/40, 42, 115, 124–125
See application file for complete search history.

(56) References Cited

U.S. PATENT DOCUMENTS

| | | | | |
|---|---|---|---|---|
| 5,125,406 A | * | 6/1992 | Goldstone et al. | 600/380 |
| 6,735,471 B2 | * | 5/2004 | Hill et al. | 607/2 |
| 7,840,278 B1 | * | 11/2010 | Puskas | 607/116 |
| 2006/0147492 A1 | | 7/2006 | Hunter | |
| 2006/0190053 A1 | | 8/2006 | Dobak | |
| 2007/0016097 A1 | | 1/2007 | Farquhar | |
| 2009/0259274 A1 | * | 10/2009 | Simon et al. | 607/40 |
| 2010/0063376 A1 | | 3/2010 | Kartush | |
| 2010/0087715 A1 | * | 4/2010 | Van Bommel et al. | 600/301 |
| 2010/0145178 A1 | * | 6/2010 | Kartush | 600/380 |
| 2011/0245647 A1 | * | 10/2011 | Stanislaus et al. | 600/380 |

* cited by examiner

*Primary Examiner* — Linda Dvorak
*Assistant Examiner* — Brian M Antiskay
(74) *Attorney, Agent, or Firm* — Perkins Coie LLP

(57) ABSTRACT

An endotracheal tube usable for intraopertive monitoring of the laryngeal nerve. The endotracheal tube includes at least one electrical contact that is movable along and about an exterior sidewall of the endotracheal tube and connected to the exterior sidewall by a connector when the electrode is placed in a position to optimize the conductivity between the nerve being monitored and the electrical contact. The electrical contact may be connected using a locking tube, tape, adhesive, etc.

17 Claims, 8 Drawing Sheets

ENDOTRACHEAL TUBE WITH A SELECTIVELY POSITIONAL ELECTRODE

CLAIM OF PRIORITY UNDER 35 U.S.C. §119

None.

CLAIM OF PRIORITY UNDER 35 U.S.C. §120

None.

REFERENCE TO CO-PENDING APPLICATIONS FOR PATENT

None.

BACKGROUND

1. Field

The technology of the present application relates generally to endotracheal tubes with electrodes to facilitate nerve monitoring, and more specifically, to an endotracheal tube that includes an electrode that is selectively positional along a length of the tube and capable of being fixed after positioning of the tube to facilitate monitoring of the laryngeal nerve.

2. Background

The recurrent or inferior laryngeal nerve (generically referred to as laryngeal nerve herein) provides connection between the brain and the larynx. The laryngeal nerve provides motor function and sensation to allow, for example, speech. Damage to the laryngeal nerve may result in changes to speech patterns, pitch, tone, or even muteness in extreme cases.

Referring to FIG. 1A, the left and right laryngeal nerves 1(L), 1(R) branches from the associated left and right vagus nerves 2(L), 2(R) and descends through the neck 3. The left laryngeal nerve 1(L) extends under the aorta 4 and rises up the neck between the trachea 5 and esophagus 6. The right laryngeal nerve 1(R) extends around the right subclavian 7 artery and rises up the neck between the trachea 5 and esophagus 6.

Due to its location and length, the laryngeal nerve 1(L), 1(R) is susceptible to damage during surgical procedures in the neck. Laryngeal nerve paralysis is most associated with thyroid and related surgeries, but is possible during other procedures around the neck, such as, for example, surgery associated with the cervical spine.

Referring to FIG. 1B, the anatomy associated with the larynx 7 is provided. The larynx is generally found anterior to the neck approximate cervical spine vertebrae C3-C6. The laryngeal nerves extend along the trachea 5 to the larynx. The muscles of the larynx are generally innervated by the recurrent laryngeal nerve 1(L) and 1(R). The cricothyroid muscles 8, however, are innervated by the superior laryngeal nerve 9, of which only one portion is shown in FIG. 1B.

Because damage is possible during surgery, many surgical procedures monitor the laryngeal nerves 1(L), 1(R), and 9, and possibly other nerves, during the surgery to alert a surgeon to damage or potential damage to the nerve as well as to help locate the nerve intraoperatively. Generally, devices having electrodes are used to intraoperatively monitor the laryngeal nerve. Some of these devices include devices inserted into the upper pharynx, endotracheal tubes with one or more fixed electrodes, and surface electrodes attached to the tracheal tube. None of these solutions are perfect solutions and each may have one or more drawbacks. For example, endotracheal tubes with one or more fixed electrodes are generally designed for typical anatomy and the electrode is not optimally placed for any particular surgical patient. Thus, against this background, it would be desirous to provide an endotracheal tube that would allow an electrode to be selectively placed and fixed at a location that optimized the conductivity between the electrode and the laryngeal muscles innervated by the laryngeal nerve.

SUMMARY

Embodiments disclosed herein address the above stated needs by providing a method for selectively placing an electrode along an endotracheal tube. The method includes inserting the endotracheal tube and positioning an electrode in a first position. The connectivity between the monitored nerve and electrode is measured and it is determined whether the connectivity is optimized or satisfactory. If the connectivity is not sufficient, the electrode is moved. Once it is determined that the position of the electrode satisfies certain criteria, the electrode is fixed in position.

Other embodiments disclosed herein provide an apparatus for intraoperatively monitoring nerves. The apparatus includes an endotracheal tube having an interior and exterior sidewall and an electrode. The electrode is selectively positionable along and about a longitudinal axis of the endotracheal tube to optimize the position of the electrode. Once the position is optimized or satisfactory, the electrode is fixable at the position.

DETAILED DESCRIPTION

The technology of the present application will now be described with reference to the attached figures. While the technology of the present application is described with reference to measuring electromyography or EMG activity from the muscles innervated by the laryngeal nerve, one of ordinary skill in the art will recognize on reading the disclosure that other nerves may be monitored using the technology of the present application. Moreover, the technology of the present application will be described with reference to particular exemplary embodiments. The word "exemplary" is used herein to mean "serving as an example, instance, or illustration." Any embodiment described herein as "exemplary" is not necessarily to be construed as preferred or advantageous over other embodiments unless specifically indicated as such. Thus, the examples provided should be considered illustrative of the technology of the present application and not limiting.

Figure 1A:
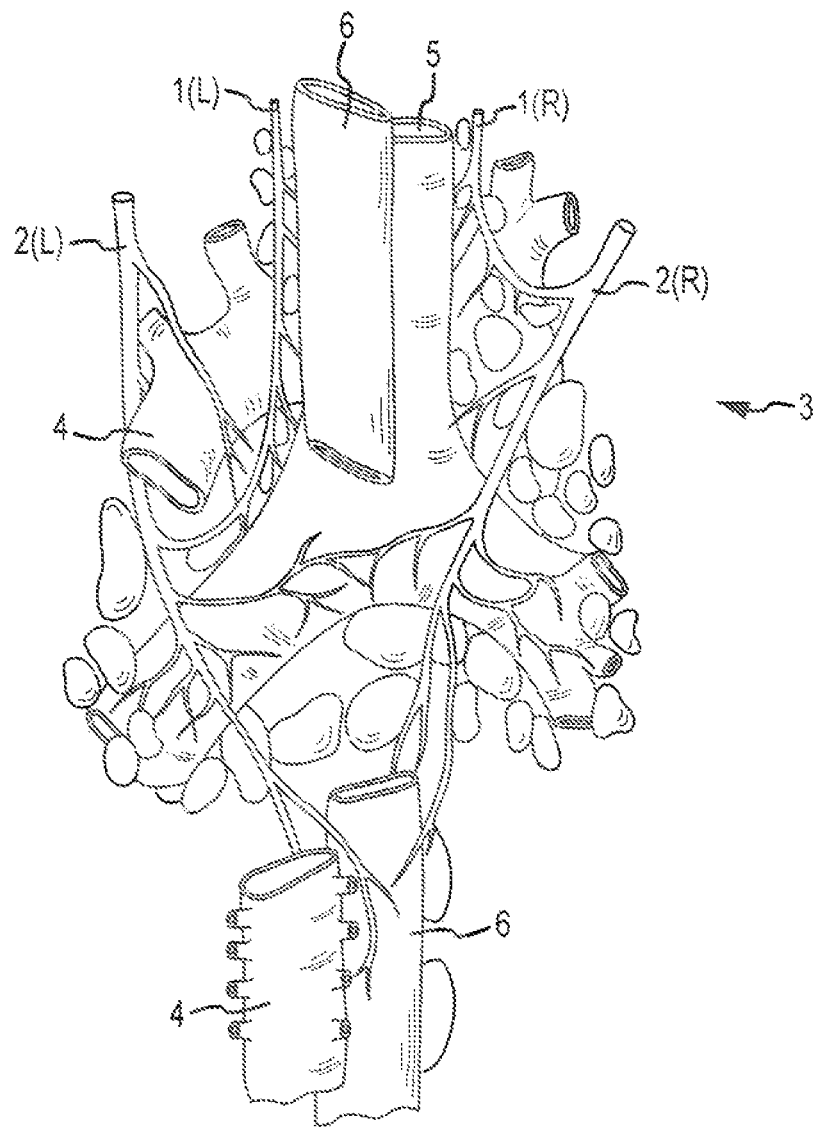
FIG. 1A is a partial view of anatomy in which the technology of the present application would be used.
Figure 1B:
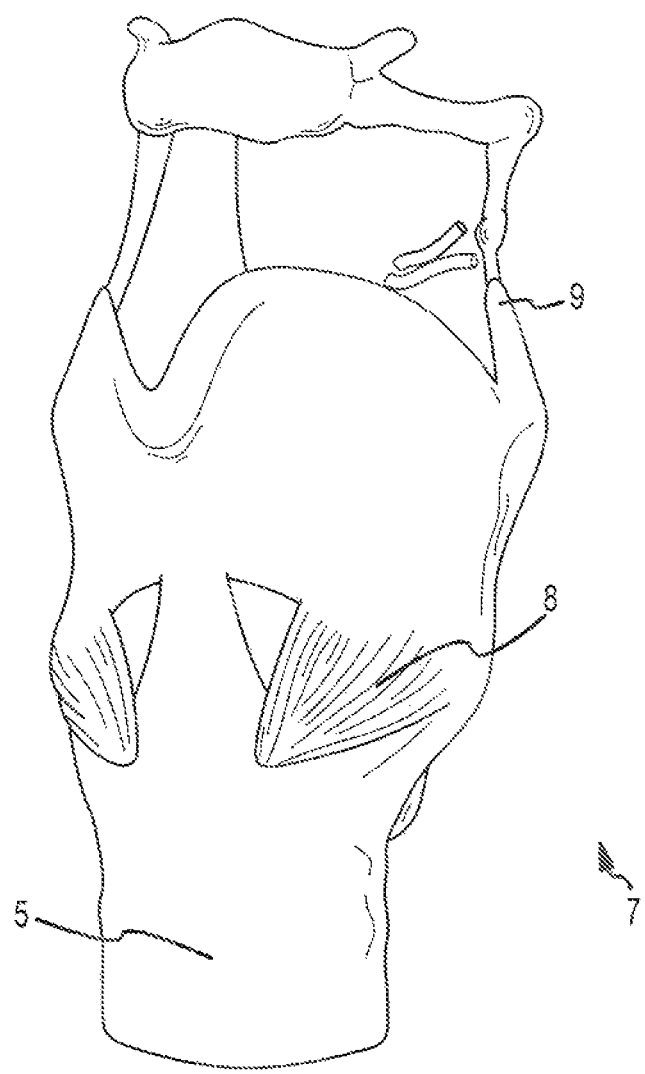
FIG. 1B is a partial view of anatomy in which the technology of the present application would be used.
Figure 2:
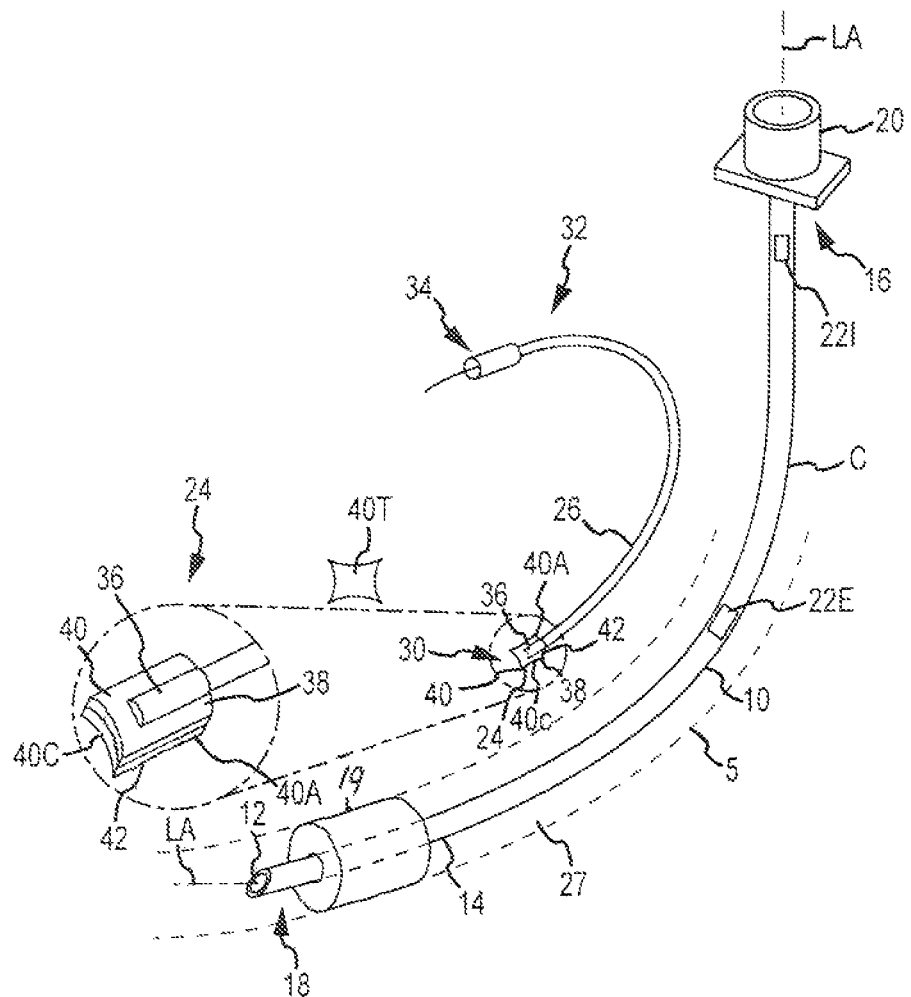
FIG. 2 is a partially exploded perspective view of an endotracheal tube consistent with the technology of the present application.

Referring now to FIG. 2, an endotracheal tube 10 consistent with the technology of the present application is shown. Endotracheal tube 10 is shown generally cylindrical to match the anatomy of the trachea of the patient. For reference, a longitudinal axis LA extends through the geometric center of endotracheal tube 10 in this exemplary embodiment. Endotracheal tube 10 includes at least one interior sidewall 12 and at least one exterior sidewall 14. Endotracheal tube 10 may be comprised of a plurality of interior and exterior sidewalls 12 and 14 joined together to form endotracheal tube 10. Endotracheal tube 10 includes a proximal end 16 adapted to remain exterior to a patient and a distal end 18 adapted to be inserted into the trachea of a patient during surgery. Proximal end 16 is coupled to a manifold 20 that is attachable to a ventilator as is conventionally known in the art but not otherwise explained herein. Endotracheal tube 10 defines an interior space 28 as shown best in FIG. 3. Interior space 28 extends from the proximal end 16 to the distal end 18. A gap 27, or space, is formed between the at least one exterior sidewall 14 of the endotracheal tube and trachea 5 of the patient. The trachea 5 is shown in phantom in FIG. 2 for reference.

An inflatable cuff 19 resides on endotracheal tube 10 towards the distal end 18. The inflatable cuff 19 is deflated to allow the tube 10 to be placed in the trachea of the patient. Once positioned, the cuff is inflated in a conventional manner. Inflating the cuff 19 secures the position of the tube 10 in the patient's trachea 5 and provides a seal. Gap 27 extends from the proximal end 16 of the endotracheal tube 10 to the inflated cuff 19.

Figure 3:
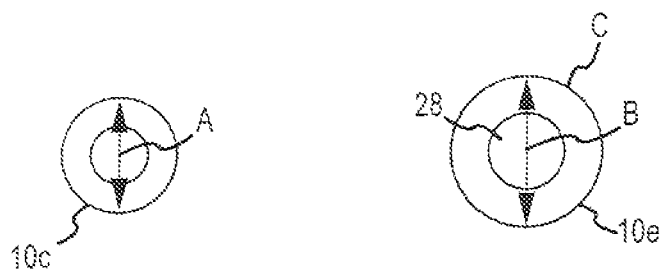
FIG. 3 is a cross-sectional view of the endotracheal tube of FIG. 2 in a collapsed configuration and an expanded configuration.

Optionally, as shown by FIG. 3, endotracheal tube 10 may be expandable and collapsible instead of or in addition to having the inflatable cuff 19. FIG. 3 shows a cross-sectional view of a collapsed endotracheal tube 10c having a first diameter A and a cross-section view of an expanded endotracheal tube 10e having a second diameter B greater than first diameter A. Expanded endotracheal tube 10e has a diameter such that exterior sidewall 14 fits snugly within the tracheal wall of the patient. In the expanded configuration, the tube 10 would function similar to the inflated cuff by securing the position of the tube and forming a seal.

Referring back to FIG. 2, the electrode 24 and cable 26 may be inserted directly into interior space 27 at the proximal end of endotracheal tube 10. Thus, cable 26 would extend along the exterior sidewall 14 of the endotracheal tube 10 in the trachea 5. Alternatively, endotracheal tube 10 may have an ingress 22I and an egress 22E along a length of endotracheal tube 10. Thus, instead of extending along the outer sidewall 14 over the entire length of the trachea 5, cable 26 would extend along the inner sidewall 12 from the ingress 22I to the egress 22E.

Cable 26 may be any conventional wire, such as a twisted pair, coaxial cable, etc. Cable 26, as shown, is encased in a protective sheath. Cable 26 has a distal end 30 to which electrode 24 is attached and a proximal end 32 to which a connector 34 is attached. Connector 34 couples to a processor for intraoperative monitoring of the laryngeal or other nerve as is generally known in the art and will not be explained herein. Cable 26 has a length sufficient to allow electrode 24 to be placed as required by the technology of the present application.

Electrode 24 comprises the electrical contact 36 and substrate 38. Substrate 38 has a first side 40 to which electrical contact 36 is attached and a second side 42 opposite the first side 40. Cable 26 is electrically coupled to electrical contact 36. A coupler 40C is used to connect substrate 38 to exterior sidewall 14 of the endotracheal tube 10. Second side 42 of substrate 38 may include a bio-compatible adhesive material 40A as the coupler 40C to allow coupling electrode 24 to the exterior sidewall 14 of endotracheal tube 10. Adhesive material is one structural means, for attaching electrode 24 to endotracheal tube 10. Placing electrode 24 will be explained further below. Alternatively, tape 40T may be used as the coupler 40C to couple the electrode 24 to the exterior sidewall 14 at the determined location. Tape is another structural means for attaching electrode 24 to endotracheal tube 10. If an expandable/collapsible endotracheal tube is used, the expansion of the endotracheal tube would cause a friction fitting to secure the electrode 24 between the tracheal wall and the exterior sidewall 14. Adhesive, tape and a friction fitting are but three possible ways to selectively fix the electrode 24 to the exterior sidewall of endotracheal tube 10, and other equivalent mechanisms may be used.

Figure 4:
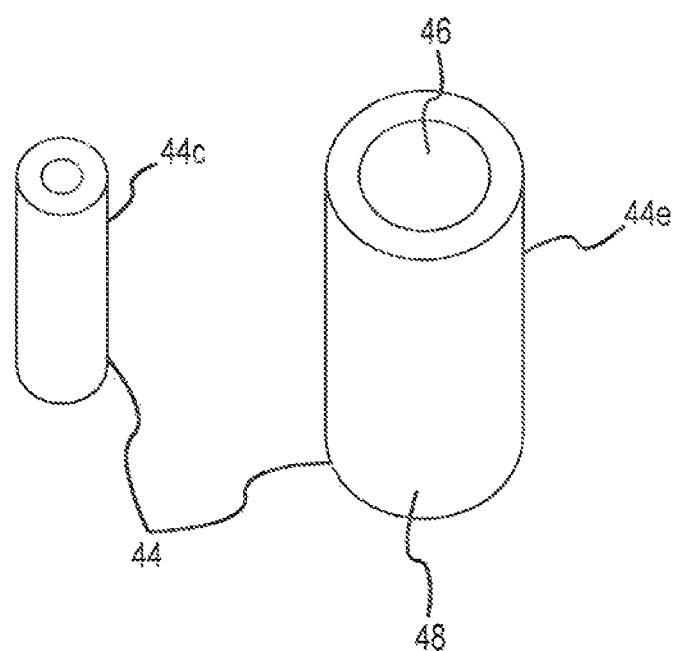
FIG. 4 is a perspective view of a locking tube consistent with the technology of the present application.

Alternatively to adhesive and/or tape, electrode 24 may be fixed in place using a locking tube 44. In this case, the electrode 24 may not be fixed to the endotracheal tube 10 as a matter of design choice. As shown in FIG. 4, locking tube 44 is expandable and collapsible having a first collapsible configuration 44c and a second expanded configuration 44e. Locking tube 44 in the first collapsible configuration 44c is insertable into gap 27 such that it may be moved into a position adjacent electrode 24 after electrode 24 is placed. As may be appreciated, the inner diameter of locking tube 44 is sufficiently sized to allow a sliding relationship to the exterior sidewall 14 of endotracheal tube 10. Once adjacent electrode 24, locking tube 44 is expanded to the second expanded configuration 44e forming at least a friction fit with the trachea 5 of the patient that secures electrode 24 in position. Locking tube 44 includes an inner passage 46 to fit around endotracheal tube 10. While shown as a tube or complete cylinder, the locking tube 44 may only partially circle endotracheal tube 10, such, as for example, a C-shaped spring clip or the like. Locking tube 44 also has at least one outer sidewall 48 configured to cooperatively engage the trachea 5 and at least one inside sidewall 49 to slidingly engage the exterior sidewall 14 of endotracheal tube 10. As can be appreciated, locking tube 44 is still another structural means for attaching electrode 24 in position. While shown as a separate component, locking tube 44 may be adapted to be permanently attached to endotracheal tube 10. For example, locking tube 44 may be a spring clip slidingly coupled about tube 10. A locking tube 44 also may include a tongue and groove arrangement as described below with reference to FIG. 6, for example.

As can be appreciated, using the adhesive, tape, locking tube, or the like (hereinafter generically referred to as "a connector") allows electrode 24 to be selectively connectable to the exterior sidewall 14 of endotracheal tube 10 or the trachea 5 of a patient. Prior to connecting electrode 24 to the endotracheal tube 10, as is explained further below, the electrode 24 may be selectively moved along the exterior sidewall 14, both along a length of endotracheal tube 10 and about a circumference C of endotracheal tube 10.

Figure 5:
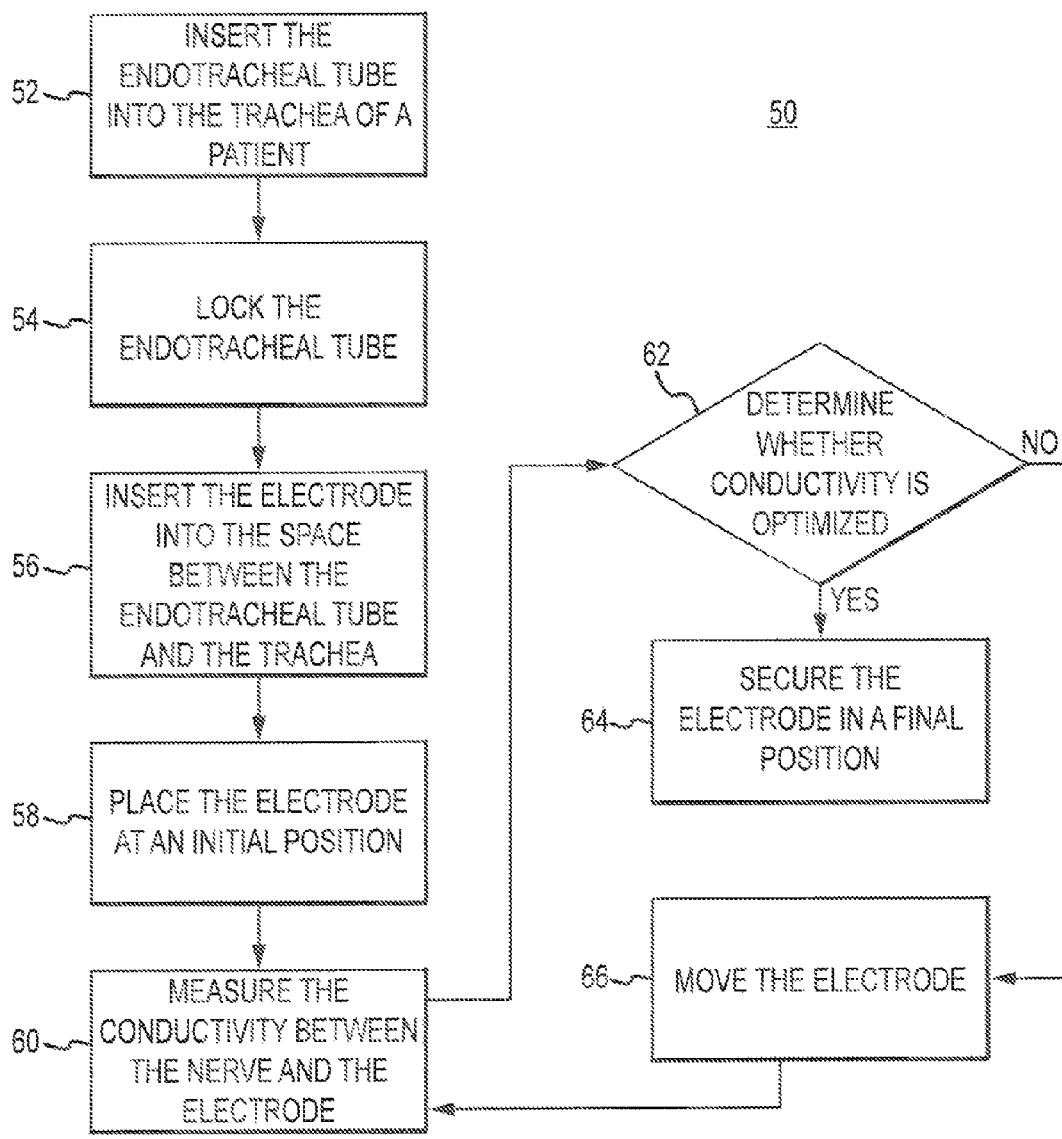
FIG. 5 is an illustrative flowchart exemplary of one method of performing operations consistent with the technology of the present application.

Referring now to FIG. 5, a flowchart 50 is provided with an exemplary method to locating an electrode 24 about an endotracheal tube 10. While flowchart 50 is provided in certain discrete steps, one of ordinary skill in the art will recognize that the steps identified may be broken into multiple steps or multiple steps in the flowchart may be combined into a single step. Moreover, the sequence of events provided by the flowchart may be altered or rearranged without departing from the technology of the present application. With that in mind, the process of locating the electrode begins during a surgical procedure with the insertion of the endotracheal tube 10 into the trachea of the patient, step 52. Placement of the endotracheal tube 10 in the trachea includes locking or securing the tube 10 in position and forming a seal, step 54. Securing the tube 10 and forming a seal typically includes inflating inflatable cuff 19, but may include expanding the endotracheal tube 10 from the collapsed configuration to the expanded configuration. Next, the electrode 24 is inserted into the space 27 between the endotracheal tube 10 and the trachea 5, step 56, and placed at an initial position, step 58. Next, the conductivity between the electrode and the laryngeal muscles is measured, step 60. The conductivity may be measured using conventional EMG. It is next determined whether the location of the electrode satisfies the conductivity requirements between the electrode and the nerve, step 62. Determining whether the location of the electrode satisfies the conductivity requirements may be referred to herein as locating the optimal location for the electrode and/or optimizing the location of the electrode, but optimization should not be construed to mean the single best location from the electrode but a position that satisfies conductivity requirements. For example, it may be determined the electrode is in an optimal location when stimulation of the muscle(s) or nerve produces a certain predetermined response; although it is possible to find the absolute best location for conductivity as well. If it is determined that the electrode is in an optimal location or a location that satisfies the conductivity requirements, the electrode 24 is secured to the exterior sidewall 14 of the endotracheal tube at the optimized or final position, step 64. Notice that in some instances, the initial position and the final position may, in fact, be identical. To facilitate securing the electrode 24 to the exterior sidewall 14 of endotracheal tube 10, the exterior sidewall 14 may be marked by the surgeon. If the electrode 24 is determined to not be in the optimal location, electrode 24 is moved, step 66, and control returns to step 60.

Securing electrode 24 may take several forms. As mentioned above, electrode 24 may be adhered to endotracheal tube 10, taped to endotracheal tube 10, or locked using a locking tube 44. Adhesive and tape may be predisposed on substrate 38 or subsequently added. The locking tube 44 may be inserted into the gap 27 about endotracheal tube 10 or predisposed about the endotracheal tube 10 and expanded to form a friction fitting to fix the electrode 44 in place.

Determining whether electrode 24 has sufficient conductivity with the associated muscle(s)/nerve(s) to be monitored may include, for example, stimulating the nerve with an electrical signal and measuring the response generated in electrode 24. The conductivity may be considered satisfactory if, for example, the voltage registered at electrode 24 exceeds a predetermined threshold. Alternatively, conductivity may be considered optimized if, for example, the change in voltage, current, etc. satisfies known optimization algorithms such as, for example, a least mean square calculation or the like.

Figure 6:
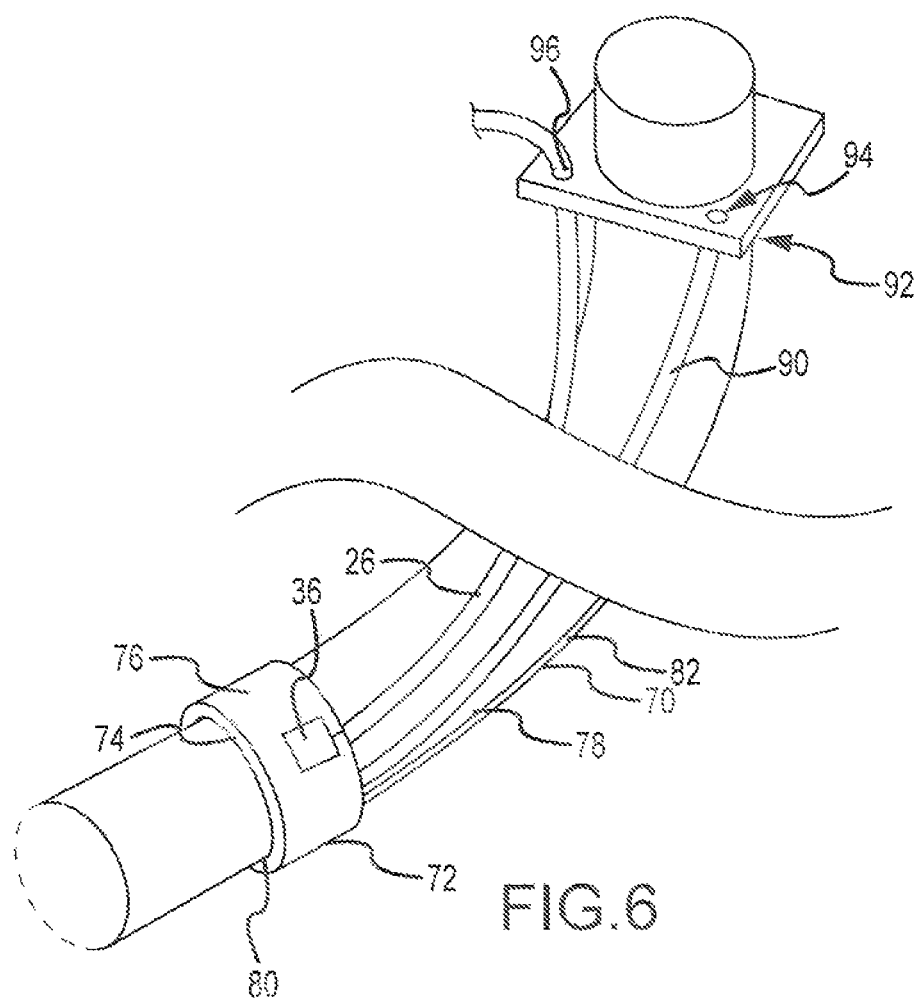
FIG. 6 is a perspective view of an endotracheal tube consistent with the technology of the present application.

Referring now to FIG. 6, a partial view of an endotracheal tube 70 is provided. The endotracheal tube 70 is substantially the same as endotracheal tube 10 described above and will not be further described herein. Endotracheal tube 70 includes a fitting 72. Fitting 72 is similar to electrode 24 above. Fitting 72 includes a first surface 74 adjacent the exterior sidewall 78 of endotracheal tube 70 and a second surface 76 opposite the first surface. Electrical contact 36 is attached to second surface 76. Cable 26 attaches to electrical contact 36 and extends along the exterior or interior sidewall of endotracheal tube 70.

Fitting 72 is slidably coupled to exterior sidewall 78 of endotracheal tube 70. Fitting 72 may comprise a material, such as, for example, a mesh material, a gauze material, a plastic, a metal or metal alloy such as shape memory alloys, or the like to fit around endotracheal tube 70 such that the fitting 72 is movable along and around endotracheal tube 70. Fitting 72 may be snug fitting such that fitting 72 is friction fit to endotracheal tube 70. If friction fit to endotracheal tube 70, it is envisioned that fitting 72 would be an elastic material, although an inelastic material would be possible as well. If fitted snugly to endotracheal tube 70 by a friction fitting, fitting 72 would be movable if manipulated, but friction fit to the endotracheal tube if not manipulated. While shown as completely encompassing the circumference of entodracheal tube 70, fitting 72 may be designed to only partially encompass the circumference of endotracheal tube 70, such as, for example, a C shape as opposed to an O shape. Moreover, fitting 72 may not be friction fit to endotracheal tube 70. In these cases, cable 26, or alternatively a manipulator 90, may be used to allow a surgeon to push or pull fitting 72 up and down the length of endotracheal tube 70 and to rotate fitting 72 about endotracheal tube 70. Once fitting 72 and electrical contact 36 are positioned as desired, the cable 26 or the manipulator 90 may be anchored using an anchor 94 to a top edge 92 of endotracheal tube 70. Anchor 94 may be, for example, a clip, a pin, or the like. Alternatively cable 26 or manipulator 90 may couple to a port 96 in manifold 20 to secure the fitting 72 in the desired location.

The fitting 72 may include a protrusion 80, such as a rail, on the first surface 74 that cooperatively and slidingly engages a groove 82 on the exterior sidewall. In this case, however, a rail and groove arrangement would limit the rotational movement of fitting 72. In this case, fitting 72 may comprise a plurality of electrical contacts 36 or an electrical contact that extends more about the circumference of endotracheal tube 70 to accommodate the reduced rotation.

Figure 7:
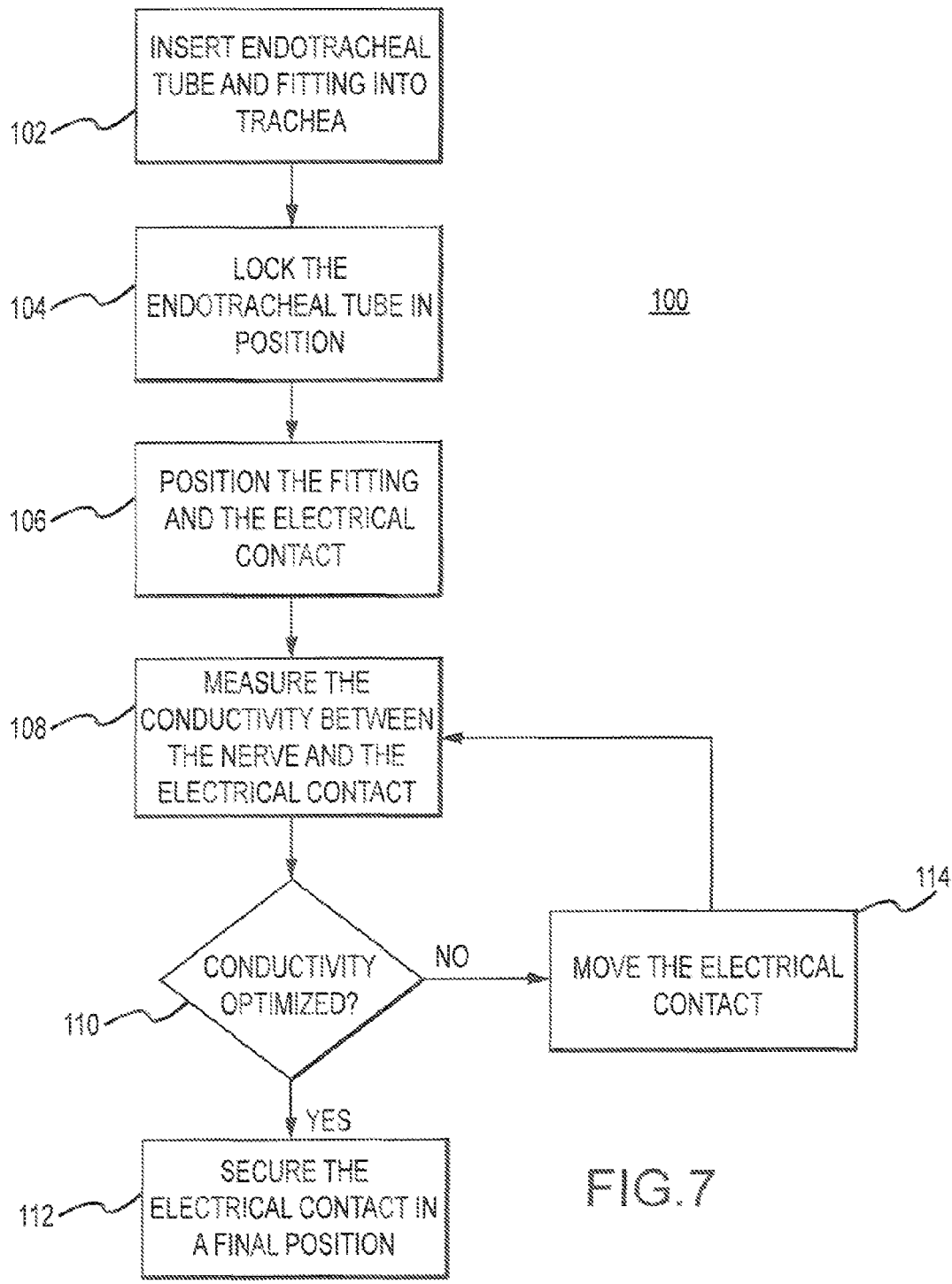
FIG. 7 is an illustrative flowchart exemplary of one method of performing operations consistent with the technology of the present application.

Referring now to FIG. 7, a flowchart 100 is provided with an exemplary method to locating fitting 72 and electrical contact 36 about an endotracheal tube 70. While flowchart 100 is provided in certain discrete steps, one of ordinary skill in the art will recognize that the steps identified may be broken into multiple steps or multiple steps in the flowchart may be combined into a single step. Moreover, the sequence of events provided by the flowchart may be altered or rearranged without departing from the technology of the present application. With that in mind, the process of locating the electrode begins during a surgical procedure with the insertion of the endotracheal tube 70 and fitting 72 into the trachea of the patient, step 102. Placement of the endotracheal tube 70 in the trachea includes locking or securing the tube 70 in position and forming a seal, step 104. Securing the tube 70 and forming a seal typically includes inflating inflatable cuff 19, but may include expanding the endotracheal tube 70 from the collapsed configuration to the expanded configuration. Next, and if necessary, the fitting 72 and electrical contact 36 are positioned in a first location, step 106. Placing the fitting 72 and the electrical contact 36 in the first location may be accomplished in conjunction with inserting the endotracheal tube 70 into the patient's trachea. However, the surgeon may move the fitting 72 and the electrical contact 36 to a more appropriate location. Next, the conductivity between the electrical contact 36 and the laryngeal muscles or associated nerves is measured, step 108. The conductivity may be measured using conventional EMG. It is next determined whether the location of the electrical contact 36 optimizes the conductivity requirements or satisfies the conductivity requirements between the electrode and the nerve, step 118. As described above, optimization should not be construed to mean the single best location from the electrode but a position that satisfies conductivity requirements. For example, it may be determined the electrode is in an optimal location when stimulation of the muscle(s) or nerve produces a certain predetermined response; although it is possible to find the absolute best location for conductivity as well. If it is determined that the electrode is in an optimal location, the fitting 72 is secured in place, step 112. The fitting may be secured by, for example, anchoring cable 26 and/or manipulator 90 to the endotracheal tube or allowing the friction between fitting 72 and endotracheal tube 70 hold the fitting 72 in place. If the fitting 72 and electrical contact 36 are determined to not be in the optimal location, they are moved, step 114, and control returns to step 108.

In still another embodiment, fitting 72 may be expandable. In this case, when the fitting 72 is placed for testing or subsequent to locating the final position, the fitting 72 is expanded such that the second surface 76 is adapted to be proximate the trachea 5 of the patient, and preferably flush with the trachea 5 of the patient. Expandable fitting 72 may be fitted in sliding relation to the endotracheal tube 70 such as, for example, a washer around a pipe or the like. Expandable fitting 72 may be prearranged on endotracheal tube 70 or placed on endotracheal tube 70 after tube 70 is placed in the trachea 5 of the patient. Expandable fitting 72 may be formed of an expandable mesh material, such as a metal, metal alloy, composite, plastic, or other biologically compatible material that is expandable. For example, expandable fitting 72 may be made from titanium, a shape memory alloy, or the like. Also, while shown as encircling tube 70, expandable fitting 72 may not be a complete circle or cylinder that encircles tube 70, but rather a C shape, a U shape, a J shape or the like that hooks around tube 70. Moreover, expandable fitting 72 may be inflatable similar to inflatable cuff 19.

Figure 8:
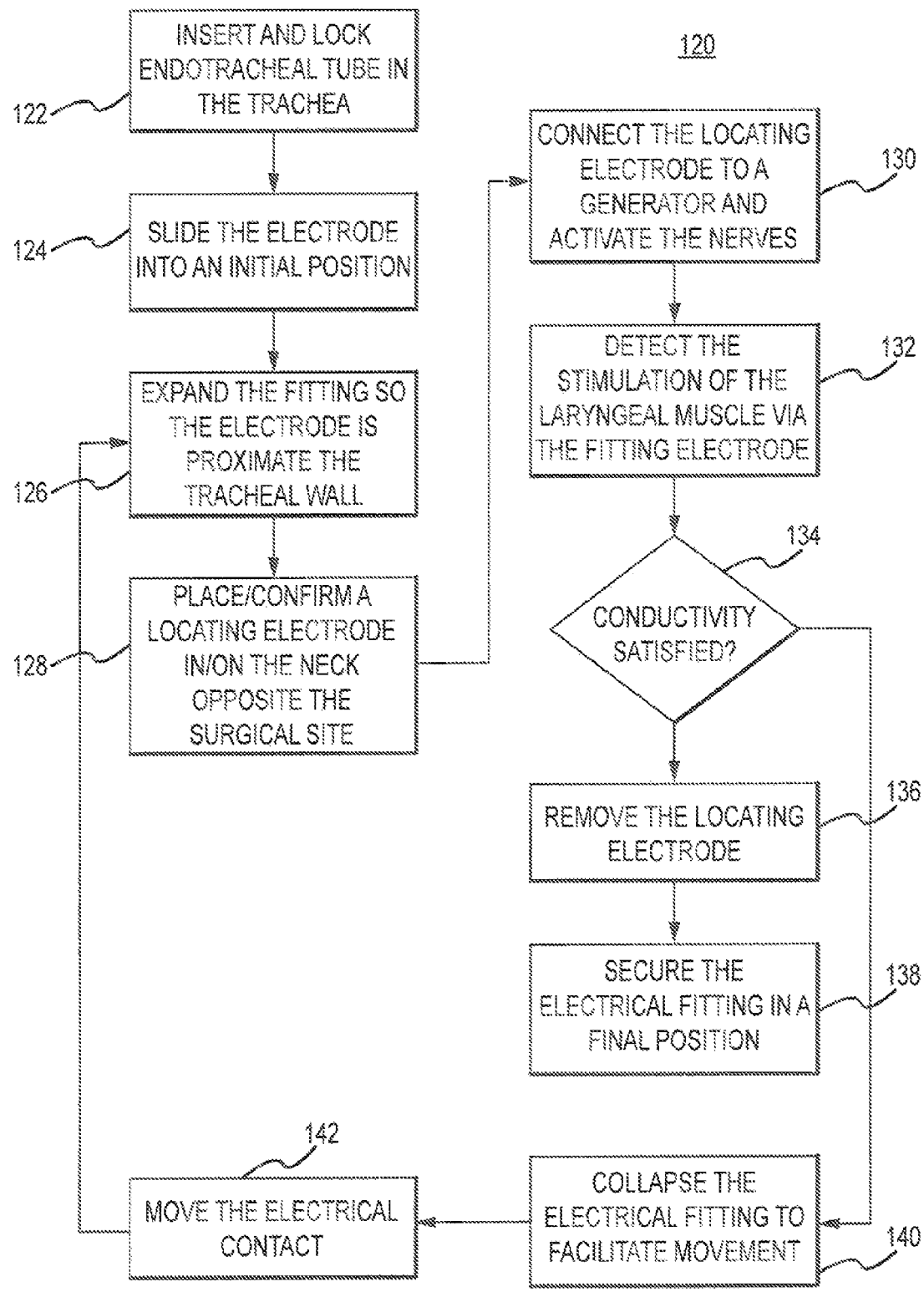
FIG. 8 is an illustrative flowchart exemplary of one method of performing operations consistent with the technology of the present application.

In some instances, the above apparatus and method are used where the monitored nerve is exposed and located during surgery. For example, during thyroid surgery, the laryngeal nerves are located and the nerve is stimulated to find an optimal or satisfactory placement of the electrode. However, in other surgeries, such as, for example, spinal surgery related to the cervical spine, the laryngeal nerve may not be located nor exposed. Referring now to FIG. 8, a flow chart 120 is provided that is useful when the associated nerves are not exposed or located, but may be used when the associated nerves are exposed or located as well. While flow chart 120 is described in certain discrete steps, one of ordinary skill in the art will recognize that the steps identified may be broken into multiple steps or multiple steps in the flowchart may be combined into a single step. Moreover, the sequence of events provided by the flowchart may be altered or rearranged without departing from the technology of the present application. With that in mind, the process begins by placing an endotracheal tube in the trachea of a patient and securing the tube by, for example, expanding cuff 19, step 122. Next the electrode is slid into an initial position, step 124. In the case of expandable fitting 72, the fitting may be positioned on the proximate end of endotracheal tube 70 and moved along the exterior surface 78 towards the distal end of tube 70 until located approximately where the anesthesiologist or surgeon believes the electrode should be placed. Expandable fitting 72 is next expanded to fix the location of the electrode proximate the trachea of the patient, step 126. The expansion may be by allowing a spring C clip to expand, allowing a mesh material to expand, allowing a shape memory alloy to expand, inflating the expandable fitting, or the like. A stimulating electrode is placed (or confirmed if already placed) on the neck opposite the surgical site, step 128. The stimulating electrode may be a surface electrode or a needle electrode. In the present application, electrode should be generically construed to mean either a single electrode or an electrode pair. Thus, the stimulating electrode is an electrode pair comprising an anode and a cathode in this particular exemplary embodiment whereas the electrode on fitting 72 may be a single electrode. The stimulating electrode is connected to a generator and stimulated to activate the appropriate nerves, step 130. For example, a stimulating electrode that is a surface electrode may activate the phrenic nerve and subsequently the recurrent laryngeal nerve. The activation of the recurrent laryngeal nerve would innervate the laryngeal muscle that would fire or react. The firing of the laryngeal muscle is detected by the electrode in, for example, expandable fitting 72, step 132. Based on the response measured by the electrode, it is determined whether the conductivity requirements are satisfied by the present orientation of fitting 72, step 134. If the conductivity requirements are satisfied, the stimulating electrode is removed, step 136, and the fitting 72 is secured in place (which may already have been accomplished by the expansion), step 138. Otherwise the expandable fitting 72 is collapsed, step 140, and moved, step 142. Once moved, control returns to step 126.

In many instances, electrodes associated with the endotracheal tube may be on a surgical side of the neck and a non-surgical side of the neck. In the above example, once the fitting 72 for the surgical side of the neck is positioned, a surgeon may want to remove any electrodes on the non-surgical side, which may include deflating the associated expandable fitting or the like. However, the surgeon or anesthesiologist may wish to monitor both the surgical and non-surgical side of the neck. For example, in some instances, the anesthesiologist may want to monitor nerve and muscle function bilaterally after intubation before staring a procedure to identify typical and, perhaps more importantly, atypical function. Moreover, in some instances, an anesthesiologist may elect to monitor both the surgical and non-surgical sides of the neck as there have been reports in cases where there is underlying, undiagnosed nerve/muscle dysfunction prior to the patient going to surgery that have been detected by required pre-operative ear, nose, and throat (ENT) exams relating to functionality. Stimulating and monitoring both sides of the neck may allow identification of nerve/muscle dysfunction prior to initiating a surgical procedure such that a surgeon may elect to approach the surgery from the dysfunctional side, instead of the more typical side, to avoid a potential injury to the typical nerves/muscles, which could be devastating.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The steps of a method or algorithm described in connection with the embodiments disclosed herein may be embodied directly in hardware, in a software module executed by a processor, or in combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for inserting an elongated, flexible tube in a trachea of a patient and selectively placing an electrode initially detached from the elongated, flexible tube to facilitate monitoring at least one nerve during a surgical procedure, the method comprising:
    inserting an elongated, flexible tube in a trachea of a patient, the elongated, flexible tube having at least one interior sidewall and at least one exterior sidewall;
    positioning an electrical contact detached from the elongated, flexible tube from a position external to the patient to an initial position internal to the patient and along the at least one exterior sidewall subsequent to inserting the elongated, flexible tube;
    measuring the conductivity between the electrical contact and the at least one nerve to be monitored;
    determining whether the position of the electrical contact optimizes the conductivity between the electrode and the at least one nerve to be monitored;
    independently moving the electrical contact detached from the elongated, flexible tube with respect to the at least one exterior sidewall of the elongated, flexible tube if it is determined that the conductivity is not optimized and repeating until the position of the electrical contact is optimized; and
    securing the electrical contact to the elongated, flexible tube in a final position when it is determined that the position of the electrical contact is optimized.

2. The method of claim 1 wherein the step of moving the electrical contact comprises moving the electrical contact along a length of the elongated, flexible tube parallel with a longitudinal axis of the elongated, flexible tube.

3. The method of claim 1 wherein the step of moving the electrical contact comprises moving the electrical contact rotationally along the at least one exterior sidewall of the elongated, flexible tube about a longitudinal axis of the elongated, flexible tube.

4. The method of claim 1 further comprising the step of:
    marking the final position on the at least one exterior sidewall of the elongated, flexible tube;
    removing the elongated, flexible tube from the trachea of the patient;
    fixing the electrical contact to the marked final position external to the patient; and
    inserting the elongated, flexible tube and fixed electrical contact into the trachea of the patient.

5. The method of claim 1 further comprising the steps of:
    stimulating the at least one nerve to be monitored by the electrical contact;
    detecting the electrical impulse using the at least one electrical contact; and
    determining the final position to optimize the conductivity between the electrical contact and the at least one nerve to be monitored when the detected electrical impulse exceeds a predetermined threshold.

6. The method of claim 1 wherein the step of securing the electrical contact comprises using an adhesive to secure the electrical contact to the at least one exterior sidewall of the elongated, flexible tube.

7. The method of claim 1 wherein the step of securing the electrical contact comprises the step of taping the electrical contact to the at least one exterior sidewall of the elongated, flexible tube.

8. The method of claim 1 wherein the step of securing the electrical contact comprises the step of expanding a fitting on which the electrical contact is attached such that the fitting is adapted to be proximate the trachea of a patient.

9. The method of claim 8 wherein the step of expanding the fitting includes inflating the fitting.

10. The method of claim 1 wherein the step of securing the electrical contact comprises the step of moving a locking tube in the elongated, flexible tube to lock the electrical contact in place.

11. The method of claim 10 wherein the step of moving the locking tube includes the steps of inserting the locking tube in a collapsed state into a gap about the at least one exterior sidewall of the elongated, flexible tube and expanding the locking tube such that the locking tube is adapted to fit snugly against the trachea and lock the electrical contact in place.

12. A method for inserting a flexible, elongate tube and selectively placing an electrode to facilitate monitoring at least one nerve during a surgical procedure, the method comprising:
    inserting the flexible, elongate tube in a trachea, the tube having at least one interior sidewall and at least one exterior sidewall;
    subsequent to inserting the flexible, elongate tube in the trachea, separately inserting an electrical contact from a location exterior to the patient to a location interior to the patient and in the trachea between the at least one exterior sidewall and the trachea;
    measuring a conductivity between the electrical contact and the at least one nerve to be monitored;
    determining whether a position of the electrical contact optimizes the conductivity between the electrode and the at least one nerve to be monitored;
    moving the electrical contact freely both longitudinally and radially along the at least one exterior sidewall of the tube if it is determined that the conductivity is not optimized and repeating until the position of the electrical contact is optimized; and
    securing the electrical contact in a final position when it is determined that the position of the electrical contact is optimized.

13. The method of claim 12, wherein the step of separately inserting the electrical contact comprises:

introduce the electrical contact to an interior of the tube through an ingress located on a proximal end of the tube; and extracting the electrical contact from the interior of the tube to a space located between the at least one exterior sidewall and the trachea through an egress located on the tube distal of the ingress.

14. The method of claim 12, wherein securing the electrode comprises taping the electrode to the at least one external sidewall of the tube.

15. The method of claim 12, wherein securing the electrode comprises adhering the electrode to the at least one external sidewall of the tube.

16. The method of claim 12, wherein securing the electrode comprises expanding a fitting on which the electrical contact is attached such that the fitting is adapted to be proximate the trachea.

17. The method of claim 1, wherein positioning an electrical contact in an initial position along the at least one exterior sidewall subsequent to inserting the endotracheal tube comprises moving the electrical contact to the initial position by moving the electrode parallel to a longitudinal axis of the endotracheal tube and about the longitudinal axis.

* * * * *